United States Patent [19]
Herrington et al.

[11] Patent Number: 5,885,298
[45] Date of Patent: *Mar. 23, 1999

[54] PATELLAR CLAMP AND REAMER WITH ADJUSTABLE STOP

[75] Inventors: Stephen Michael Herrington, Bloomington; David Ray Brown, Leesburg; Troy William Hershberger, Warsaw, all of Ind.

[73] Assignee: Biomet, Inc., Warsaw, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 565,562

[22] Filed: Nov. 30, 1995

Related U.S. Application Data

[63] Continuation-in-part of Ser. No. 200,476, Feb. 23, 1994, abandoned.

[51] Int. Cl.⁶ .................................................. A61B 17/56
[52] U.S. Cl. ................................................................ 606/88
[58] Field of Search ................................ 606/88, 87, 86, 606/89, 96, 79, 80, 84, 85, 102

[56] References Cited

U.S. PATENT DOCUMENTS

| | | | |
|---|---|---|---|
| 4,706,660 | 11/1987 | Petersen | 606/80 |
| 4,710,075 | 12/1987 | Davison | 408/202 |
| 5,129,907 | 7/1992 | Heldreth et al. | 606/80 |
| 5,180,384 | 1/1993 | Mikhail | 606/80 |
| 5,342,364 | 8/1994 | Mikhail | 606/79 |
| 5,380,332 | 1/1995 | Ferrante | 606/79 |
| 5,536,271 | 7/1996 | Daly et al. | 606/80 |
| 5,575,793 | 11/1996 | Carls et al. | 606/80 |

*Primary Examiner*—Guy V. Tucker
*Attorney, Agent, or Firm*—Harness, Dickey & Pierce, P.L.C.

[57] ABSTRACT

A method and surgical instrument is provided for the in situ clamping engagement and reaming of the human patella bone in preparation for the installation of a patellar button prosthesis, the clamp including a rectangular frame wherein a pair of handles are mounted for parallel movement whereby to move their respective jaws into clamped engagement with the opposite faces of the patella, and a guide head defining a fixed stop; and a reaming device including a reamer shaft disposed for rotation relative to the guide head, a depth adjustment head connected to the shaft and adapted to abut the fixed stop, and a reamer blade mounted to the shaft. The shaft is provided with indicia to indicate the thickness of the patella that will remain after the resection.

17 Claims, 6 Drawing Sheets

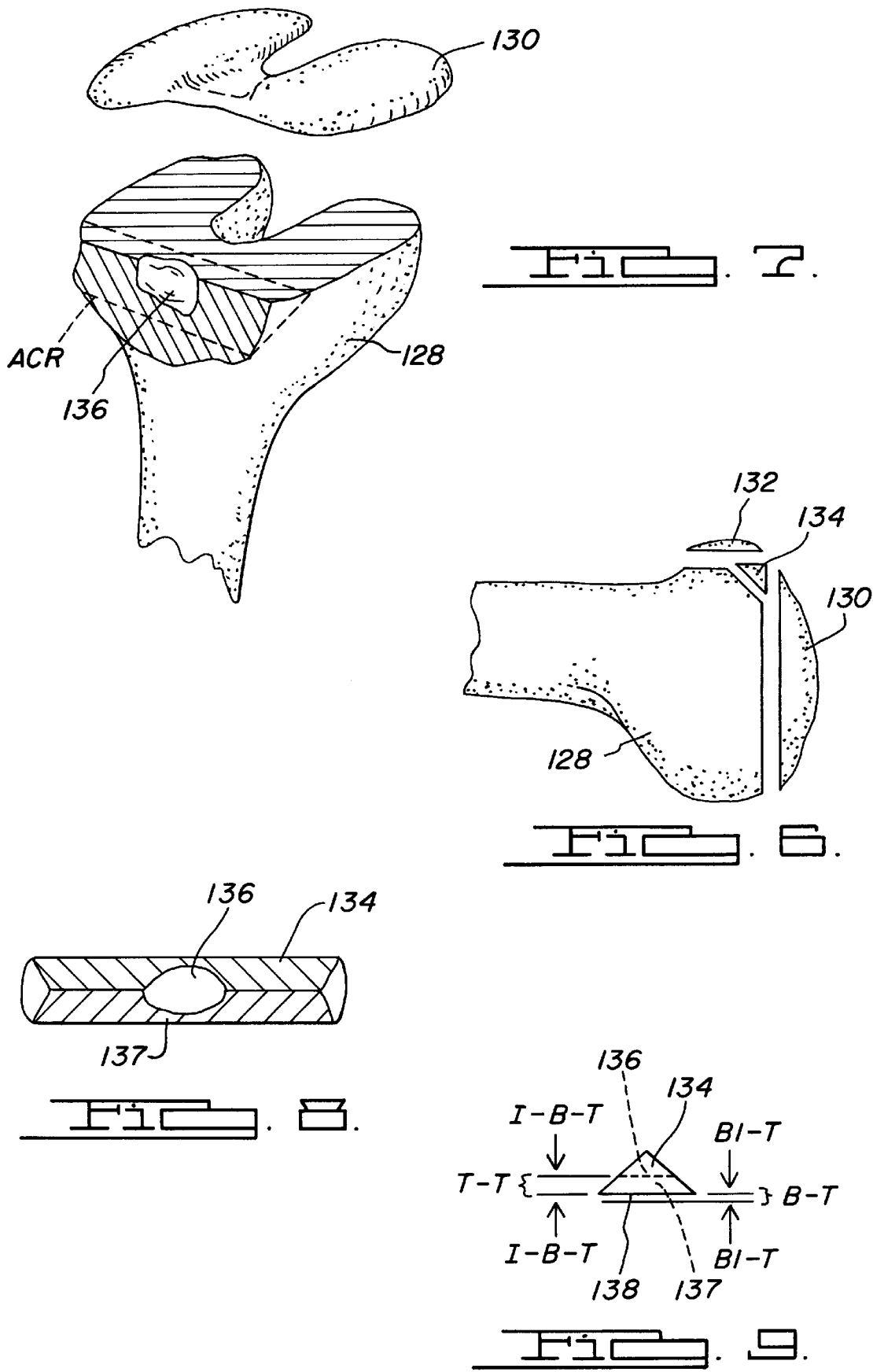

5,885,298

PATELLAR CLAMP AND REAMER WITH ADJUSTABLE STOP

CROSS REFERENCE TO RELATED APPLICATION

This is a continuation-in-part of application Ser. No. 08/200,476, filed Feb. 23, 1994, now abandoned.

BACKGROUND OF THE INVENTION

This invention relates to a method of, and a patella clamp and reamer with an adjustable stop for, in situ preparation of a patella.

During certain forms of surgery involving the knee, such as the implantation of a knee joint prosthesis, the natural patella is resected for subsequent implantation of an artificial patella component. During such a resection, various parameters must be considered in determining the desired depth of the resection. For example, the surgeon must consider the thickness of the natural patella as well as the thickness of the artificial patella components which will be implanted. In addition, the artificial patella component is typically available in different diameters so as to give the surgeon flexibility in operating on natural patellas of different sizes. However, an increase in the diameter of the artificial patella component normally results in a corresponding increase in the thickness of the artificial patella component. It is therefore often difficult for a surgeon to easily determine the depth to which a natural patella must be resected when having to consider all of these factors.

Once the surgeon has determined how much the natural patella should be resected, the patella is clamped so as to hold the patella in the fixed position. Various devices have been developed which allow the surgeon to hold the patella stationary. These devices typically involve hand operated scissors and vise-grip mechanisms. However, these devices suffer from the fact that the surgeon must maintain a clamping pressure on the patella. This application of clamping pressure may not be uniform during the resection of the patella, and possibly result in the patella being malpositioned. Accordingly, in some of the known constructions, gimbals are necessary in the jaws of such instruments to accurately position the patella during the resection procedure. Finally, some of these devices, such as the four-bar clamp which is available from Biomet, are large and bulky and therefore difficult to use and do not provide a relatively high degree of tactile feedback.

In addition, presently available instruments move a guide bushing into position against the posterior surface of the patella to clamp the patella and guide the reamer. This obscures the view of the patella such that the surgeon cannot see the patella during the resection process. This arrangement also tends to generate wear debris because the cutting blade assembly tends to contact the guide bushing.

SUMMARY OF THE INVENTION

The present invention overcomes the deficiencies in the prior art by providing an improved method and instrument for use in the implantation of an artificial patella component.

The instrument comprises a hand manipulated patella clamp including a guide head which forms part of an adjustable stop and a reaming device for performing either a resurfacing procedure or an insetting procedure for preparing a surface of a patella for a prosthetic patella implant. The patella clamp includes a pair of generally parallel upper and lower arms, each arm including a handle at one end and a jaw at the other end. The patella clamp further includes a pair of guide posts which connect the upper and lower arms together in generally parallel relation and guide the arms for parallel movement towards one another. Finally, the patella clamp includes an incrementally adjustable arrangement for locking and releasing the jaw members.

The reaming device includes an elongated shaft mountable for rotation in the guide head, a cutter blade removably connected to the shaft by means of a coupling, and a depth adjustment head connected to the shaft. The depth adjustment head is adapted to engage the guide head to accurately position the cutter blade relative to the anterior portion of the patella. The shaft has an upper end portion adapted to be driven by a surgical drill so as to cause rotation of the cutting blade assembly.

The method for the resection of a patella comprises measuring the thickness of the natural patella and then adjusting the position of the depth adjustment head relative to the reamer shaft at least partially in response to the thickness of the patella. The reamer shaft is then rotated and moved in a direction toward the patella until the depth adjustment head engages the patella clamp to prevent further movement of the reamer shaft in the direction toward the patella.

An advantage of the present invention is provision of a hand manipulated clamp which maintains two jaw members in parallel relation thereby eliminating gimbals for positioning the patella.

Another advantage of the present invention is to provide a method and apparatus for preparing a natural patella to receive an artificial patella implant which is calibrated to provide a desired degree of resection based upon the measurement of the thickness of the natural patella and the intercondylar thickness of the femur.

A further advantage of the present invention is that the patella clamp moves the reamer guide mechanism away from the posterior surface of the patella thereby enhancing the view of the patella surface being resected.

Another advantage of the present invention is that the jaws of the patella clamp maintain a uniform clamping pressure on the patella during the reaming operation and provide tactile feedback.

Yet another advantage of the present invention is the presence of a bearing arrangement utilizing a sleeve which is displaced from the patella for supporting and guiding the reamer shaft which enables close rotating tolerances to be maintained without binding.

A further advantage of the present invention is to provide a method and apparatus for preparing a natural patella to receive an artificial patella implant which is relatively easy to use and is able to firmly grip the natural patella.

BRIEF DESCRIPTION OF THE DRAWINGS

Additional advantages and features of the present invention will become apparent from the following description and appended claims, taken in conjunction with the accompanying drawings in which:

FIG. 6 is a side view of the distal end of a resected femur and selected resected portions shown in spaced-apart relation from the femur;

FIG. 7 is a perspective view of the resected femur of FIG. 6 showing the resected distal femoral portion in spaced-apart relation from the femur;

FIG. 8 is a top view of the resected anterior chamfer portion of the resected femur of FIG. 6;

FIG. 9 is a sectional view of the resected portion of FIG. 8;

DETAILED DESCRIPTION OF THE PREFERRED EMBODIMENT

It should be understood that while this invention is described in connection with a particular example, the scope of the invention need not be so limited. Rather, those skilled in the art will appreciate that the following teachings can be used in much wider variation of applications than the example specifically mentioned herein.

Figure 1:
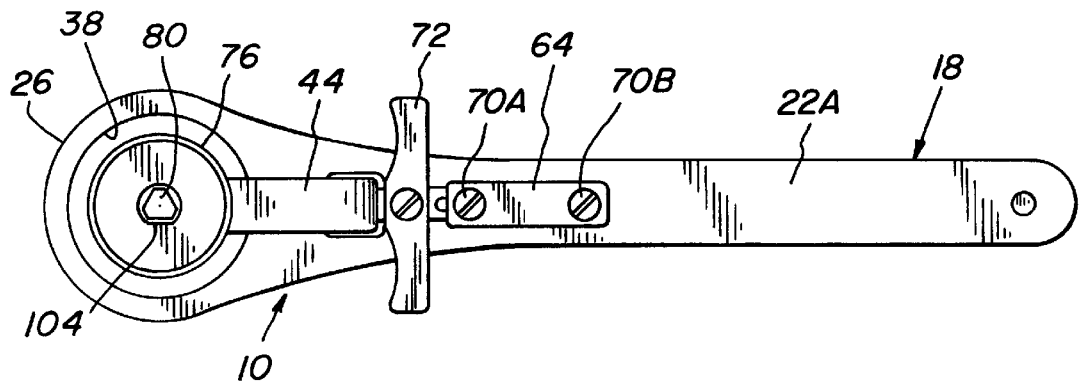
FIG. 1 is a top elevational view of a patella clamp and reamer according to the teachings of a preferred embodiment of the present invention.
Figure 2:
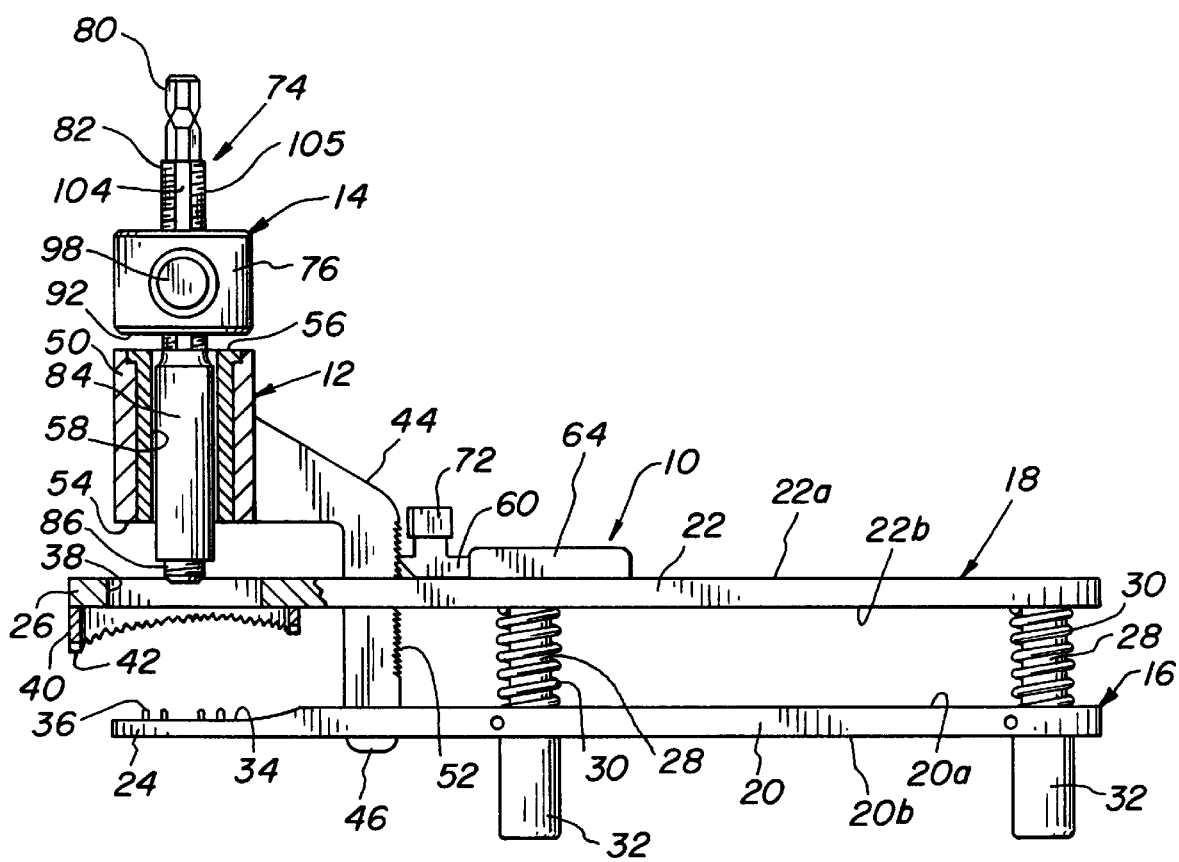
FIG. 2 is a side elevational view of the patella clamp and reamer shown in FIG. 1 with part of the reamer and clamp shown in cross-section according to the teachings of the preferred embodiment of the present invention.
Figure 3:
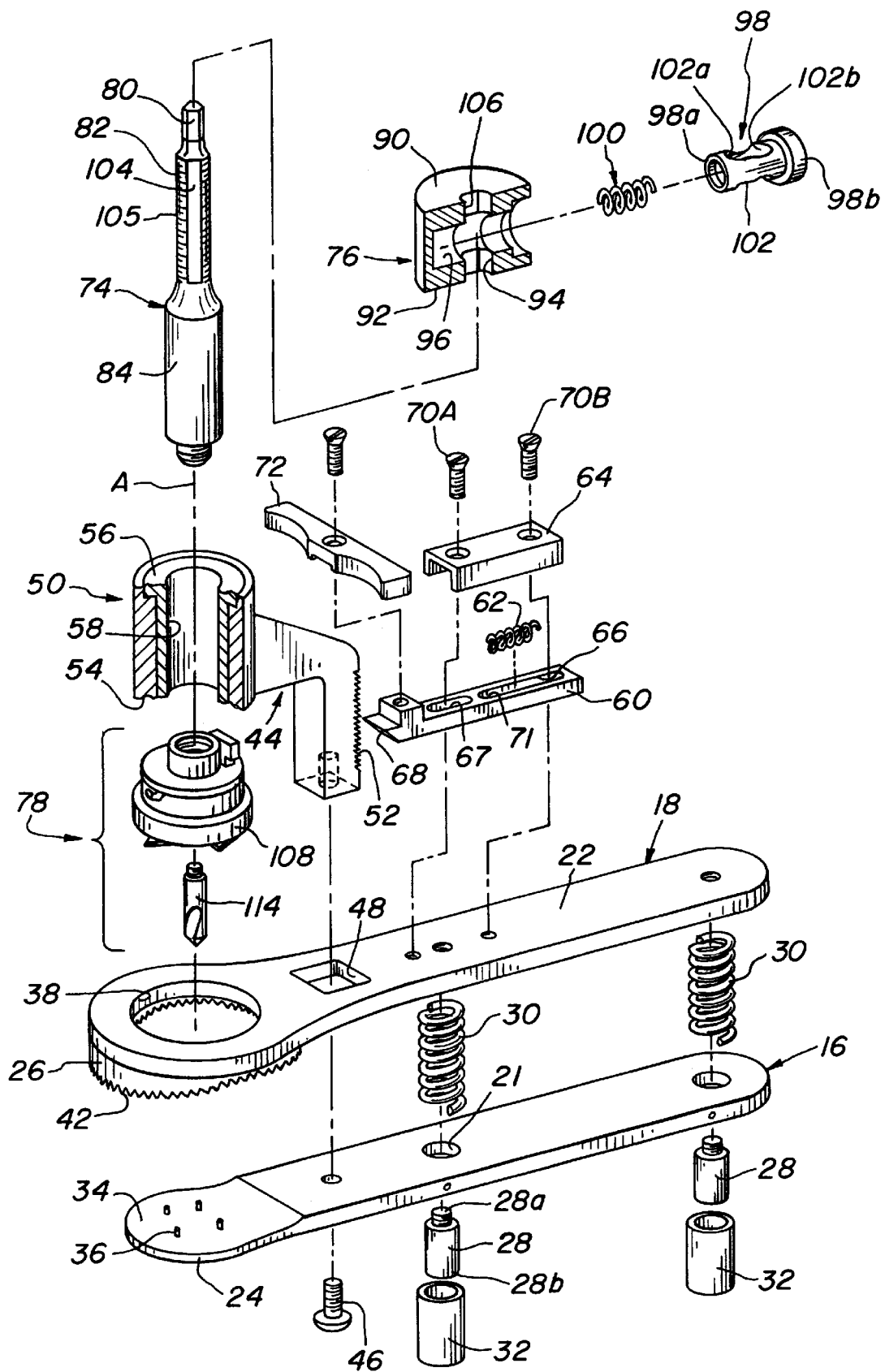
FIG. 3 is an exploded perspective view of the patella clamp and reamer shown in FIG. 1 according to the teachings of the preferred embodiment of the present invention.

Referring now to FIGS. 1–3, there is shown a surgical apparatus which is generally designated by the numeral 10. The surgical apparatus 10 is used for performing either a total resurfacing procedure or an insetting procedure on a human patella prior to receiving an artificial patella component of a knee joint prosthesis. The surgical apparatus 10 includes a patella clamp 12 and a reaming device 14. The patella clamp 12 is used to engage the natural patella in a secure fashion. The reaming device 14 is used to resect the natural patella while the natural patella is being held by the patella clamp 12.

The patella clamp 12 will now be described in greater detail. The patella clamp 12 includes lower and upper arms 16 and 18 in the form of generally flat plate-like members. The lower and upper arms 16 and 18 include a handle portion 20 and 22 at one of its ends and a jaw member 24 and 26 at the other of its ends, respectively. The patella clamp 12 further includes a pair of axial guide posts 28 for guiding the lower and upper arms 16 and 18, as well as a pair of coil springs 30 and a pair of cylindrical guide housings 32. Each of the axial guide posts 28 are encircled by one of the coil springs 30 such that the ends of each of the coil springs 30 operate against the surfaces 20a and 22b of the handle portions 20 and 22 which serve to bias the lower and upper arms 16 and 18 away from one another.

The guide posts 28 are adapted to reciprocate relative to a plurality of openings 21 in the lower handle portion 20. The guide posts 28 include a base 28a that is connected to the lower surface 22b of the upper handle portion 22 and a free end portion 28b. The guide housings 32 extends perpendicularly from the lower surface 20b of the lower handle 20 and each has an inner bore that receives the free end portion 28b and guides the respective guide post 28 for reciprocation therewithin. The guide post 28 forms a bearing member and is comprised of a material which will enhance smooth reciprocation in its guide housing 32 and obviate frictional forces from causing the lower and upper arms 16 and 18 to bind during a clamping motion. The guide posts 28 are preferably made from stainless steel while the guide housing 32 is preferably made from a composite material such as Frelon®. However, other suitable materials may be used.

The lower and upper arms 16 and 18 and the guide posts 28 form a generally rectangularly shaped assembly. In this regard, the guide posts 28 are parallel to one another and generally perpendicular to the handle portions 20 and 22. The lower and upper arms 16 and 18 are disposed in generally parallel relation and the jaw members 24 and 26 are constrained by the guide posts 28 for parallel movement towards and away from one another. This arrangement assures accurate positioning of the jaw members 24 and 26 and uniform application of clamping forces on the patella.

The lower jaw member 24 includes a slightly concave surface 34 to support the patella and is provided with one or more spikes 36 to enter and thereby grip the anterior surface of the patella. The upper jaw member 26 includes a cylindrical opening 38 and a cylindrical collar 40 arranged generally concentrically relative to a vertical axis shown at "A". Preferably, the collar 40 has an engagement face 42 which is contoured to provide a substantially continuous and uniform engagement with the posterior surface of the patella. According to a preferred embodiment, the patella engagement face 42 is formed to include V-shaped teeth for gripping the patella and ensuring that the patella does not shift during the resection.

The lower and upper arms 16 and 18 of the patella clamp 12 are adapted to be locked in a predetermined spaced relation with one another by a ratchet-type locking arrangement operating in conjunction with the upper handle portion 22. In this regard, the patella clamp 12 further comprises an L-shaped member 44 which has a lower end portion secured to the lower handle portion 20, such as by a fastener 46, a central body portion extending through an opening 48 in the upper handle portion 22 and having ratchet teeth 52 formed thereon, and a guide head 50 positioned above the upper surface 22a of the upper handle portion 22. The guide head 50 includes lower and upper end faces 54 and 56 and a cylindrical guide bore 58 that extends between the lower and upper end faces 54 and 56. The axis of the guide bore 58 and the axis "A" are generally coaxially aligned and perpendicular to the handle portions 20 and 22. According to this invention, the surface of the guide bore 58 is formed from a material having a low coefficient of friction. While metal is suitable for this purpose, the surface of the guide bore 58 may include a sleeve of Ultem® though other suitable materials may be used.

Supported on the upper surface 22a of the upper handle portion 22 is an elongated locking bar 60, a latch spring 62, and an elongated open-ended cover 64 of U-shaped cross-section that encloses the forward end of the locking bar 60 and the latch spring 62. The locking bar 60 is provided with a latch spring slot 66, an axial guide slot 67, and, at its forward end, a locking tooth 68 to interengage with the ratchet teeth 52. Threaded fasteners 70A and 70B extend through the cover 64 and into the upper handle portion 22, with the fastener 70A passing through the guide slot 67 to secure the cover 64 and the locking bar 60 to the handle portion 22. The sidewalls of the cover 64, the guide slot 67, and the fastener 70A operate to guide the locking tooth 68 of the locking bar 60 towards the ratchet teeth 52. The latch spring slot 66 includes a forward end 71. The latch spring 62 is captivated inside the cover between the fastener 70B and the forward end 71 of the latch spring slot 66. The latch spring 62 normally biases the locking tooth 68 into engagement with the ratchet teeth 52, the locking tooth 68 and ratchet teeth 52 being configured to permit the handle portions 20 and 22 to incrementally advance towards one another and the jaw members 24 and 26 into clamped engagement with the patella but operate to normally prevent reverse movement.

To release the locking tooth 68 from engagement with the ratchet teeth 52, a T-bar handle 72 is provided on the locking bar 60. The T-bar handle 72 is used to retract the locking bar 60 from the ratchet teeth 52 so as to permit movement between the lower handle portion 20 and the upper handle portion 22. This is done when it is desirable to release the patella from the jaw members 24 and 26. It will therefore be appreciated that the patella clamp 12 is configured to allow the surgeon to maintain a grip on the handle portions 20 and 22, to increase the clamping pressure on the patella, and use a finger to engage the T-bar to pull the locking bar rearwardly and cause the locking tooth 68 to be disengaged from the ratchet teeth 52.

The reaming device 14 will now be described in greater detail. The reaming device 14 includes a stepped axial reamer shaft 74, a depth adjustment head 76, and a cutting blade assembly 78 for reaming the patella. The cutting blade assembly 78 is used to ream the surface of the patella. The depth adjustment head 76 and the reamer shaft 74 are adapted to be positioned relative to one another, and the adjustment head 76 relative to the guide head 50, to accurately position the cutting blade assembly 78 relative to the patella when the patella is clamped in position by the jaw members 24 and 26. The reamer shaft 74 has an upper end 80 adapted to be engaged by a surgical drill (not shown) which is used to rotate the reamer shaft 74, a threaded upper end portion 82 adapted to engage the depth adjustment head 76, a central portion 84 adapted to rotate within the guide bore 58 of the guide head 50, and a threaded portion 86.

The depth adjustment head 76 has upper and lower end faces 90 and 92 and an axial bore 94 extending therethrough between the end faces 90 and 92 for receiving the threaded upper end portion 82 of the reamer shaft 74. The cross-section of the axial bore 94 of the depth adjustment head 76 is substantially the same as that of the upper end portion 82 of the reamer shaft 74 but dimensioned to provide a clearance fit to permit the reamer shaft 74 to move axially therewithin. The lower end face 92 of the adjustment head 76 is adapted to seat against the upper end face 56 of the guide head 50 of the patella clamp 12 so that the end faces 56 and 92 cooperate to form an adjustable stop which limits downward advance of the reamer shaft 74 and the cutting blade assembly 78. Importantly, the stop prevents the surgeon from inadvertently removing an excessive amount of material from the natural patella.

The depth adjustment head 76 also includes a locking and release arrangement whereby the depth adjustment head 76 may easily be locked in any desired position relative to the threaded upper end portion 82 of the reamer shaft 74 and/or released from threadable engagement therewith. The locking and release arrangement includes a stepped radial bore 96 in the depth adjustment head 76 that intersects and extends across the axial bore 94, an axial lock pin 98 having opposite axial ends 98a and 98b and slidably fitted in the radial bore 96, and a lock spring 100 disposed at the bottom of the radial bore 96 to normally force the lock pin 98 radially outwardly from the radial bore 96. The lock pin 98 is formed to include a transverse lock bore 102 of elliptical cross-section sized to pass the reamer shaft 74 with the long and short dimensions of the circular cross-section having a flat 104 respectively extending in the direction of and transverse to the radial bore 96. The long dimension of the lock bore 102 constitutes a first bore wall 102a facing in a direction radially outwardly of the radial bore 96 and a second bore wall 102b facing in a direction radially inwardly of the radial bore 96. Importantly, the bore wall 102a is formed with a lip or thread which is normally biased by the lock spring 100 into locked engagement with the thread on the upper end portion 82 of the reamer shaft 74.

To incrementally adjust the position of the depth adjustment head 76 relative to the reamer shaft 74, or release the engagement, the surgeon applies an inwardly directed force against the end 98b of the lock pin 98 thereby forcing the end 98a further inward in the radial bore 96. As a result, the thread formed on the wall 102a of the Lock pin 98 is moved from engagement with the thread on the reamer shaft 74 and the reamer shaft 74 is released for movement in the axial bore 94 relative to the depth adjustment head 76. Upon removal of the force against the end 98b of the lock pin 98, the lock spring 100 forces the lock pin 98 back into engagement with the thread on the reamer shaft 74.

During rotation of the reamer shaft 74, it is preferable that the depth adjustment head 76 does not rotate relative to the upper end portion 82 of the reamer shaft 74 thereby causing the preset spacing between the lower end face 92 of the depth adjustment head 76 and the patella to change. Accordingly, the upper end portion 82 of the reamer shaft 74 has a flat 104 formed with measurement settings 105 thereon and the axial bore 94 is formed to include a flat 106. The flats 104 and 106 operate to key the measurement settings 105 relative to the lock pin 98 and prevent relative rotation between the depth adjustment head 76 and the reamer shaft 74. The measurement settings 105 on the reamer shaft 74 correlate the distance between the upper end face 56 of the guide head 50 and the lower jaw member 24 in terms of the amount of the natural patella that will be left after resection. In particular, the measurement settings 105 can be related to the thicknesses of the natural patella before resection as well as the intercondylar thickness of the femur before or after resection as shown below in FIGS. 6–9 and as described with respect thereto.

The location of the measurement settings 105 on the reamer shaft 74 are selected to correspond to the thickness of the natural patella as measured by the surgeon. This enables the surgeon to select the proper measurement setting 105 by simply measuring the thickness of the patella. For example, if the surgeon determines that the thickness of the natural patella is 23 mm., the surgeon would adjust the depth adjustment head 76 to the measurement setting 105 identified as 23 mm. The length of the reamer shaft 74, as well as the height of the cutting blade assembly 78, is such that the natural patella is reamed to the desired depth once the depth stop head 76 engages the upper end face 56 of the guide head 50 such that the proper amount of bone remains after resection. While the thickness of artificial patella components vary depending on their diameter, the height of the cutting blade assembly 78 is selected to be greater for a thicker patellar implant and is thinner for a thinner patellar implant. For example, if the natural patella is determined to be 23 mm in thickness and a medium diameter patellar implant is used which has thickness of 9 mm, then placing the depth adjustment head 76 at 23 mm will leave 14 mm of bone remaining in the cavity formed in the natural patella. However, if a large diameter patellar implant is selected which has a thickness of 10 mm, then placing the depth adjustment head 76 at 23 mm will leave 13 mm of bone remaining in the cavity formed in the natural patella.

It has also been determined that it is desirable to adjust the depth of reaming in response to the intercondylar thickness of the femoral component of a knee joint prosthesis. This is because selecting the depth of the resection of the patella based solely on the thickness of the patella does not place the remaining natural patella, with the artificial patella component attached, at the same anatomical position as before surgery. In particular, because the resected intercondylar thickness of the femur is not the same as the intercondylar thickness of the femoral component, the quadriceps tendon often is not placed at the same location (typically increasing forces at 45° of flexion) after implantation as before the knee joint is replaced. Accordingly, to replicate the kinematics of the knee prior to joint replacement, it is desirable to adjust the depth to which the patellar implant is placed into the natural patella so that the quadriceps tendon will be placed in the same anatomical position after joint replacement as it was before joint replacement.

To adjust the depth of reaming to accommodate for the intercondylar thickness of the femoral component, the location of measurement settings 105 on the reamer shaft 74 may be determined as follows:

Equation (1):

Location of measurement settings=PT+ST+($IT_{femur}$−$IT_{implant}$) 105 on reamer shaft 74 where:

PT=thickness of natural patella (in mm.)

ST=thickness of saw blade used in anterior femoral resection (in mm.)

$IT_{femur}$=resected intercondylar thickness of the femur (in mm.)

$IT_{implant}$=intercondylar thickness of implant femoral component (in mm.)

Under certain assumptions, this equation can be simplified such that the location of the measurement settings 105 on the reamer shaft 74 depend only on the thickness of the natural patella and the intercondylar thickness of the femur. These assumptions include assuming that the intercondylar thickness of the femoral component of the knee joint prosthesis is constant for all sizes of implants (at approximately 3.5 mm) which is generally true for the majority of the knee joint prostheses available from Biomet. In addition, an assumption can be made that the thickness of the saw blade used in the anterior resection of the femur is about 1.5 mm. This is because the cutting blocks which are typically used to perform this resection, such as those available from Biomet, specify a blade thickness of 1.5 mm.

If these assumptions are made, the location of the measurement settings 105 on the reamer shaft 74 are determined by the following equation:

Equation (2):

Location of measurement settings PT+$IT_{femur}$−2 mm 105 on reamer shaft 74 where:

PT=thickness of natural patella (in mm.)

$IT_{femur}$=resected intercondylar thickness of the femur (in mm.)

With this simplified equation, the surgeon can simply adjust the depth adjustment head 76 to a position on the reamer shaft 74 such that the measurement setting 105 chosen is equal to the thickness of the natural patella plus the intercondylar thickness of the femoral component of the knee joint prosthesis less 2 mm. If either of the above assumptions are not accurate for the particular implant being used, then Equation (1) should be applied.

Figure 4:
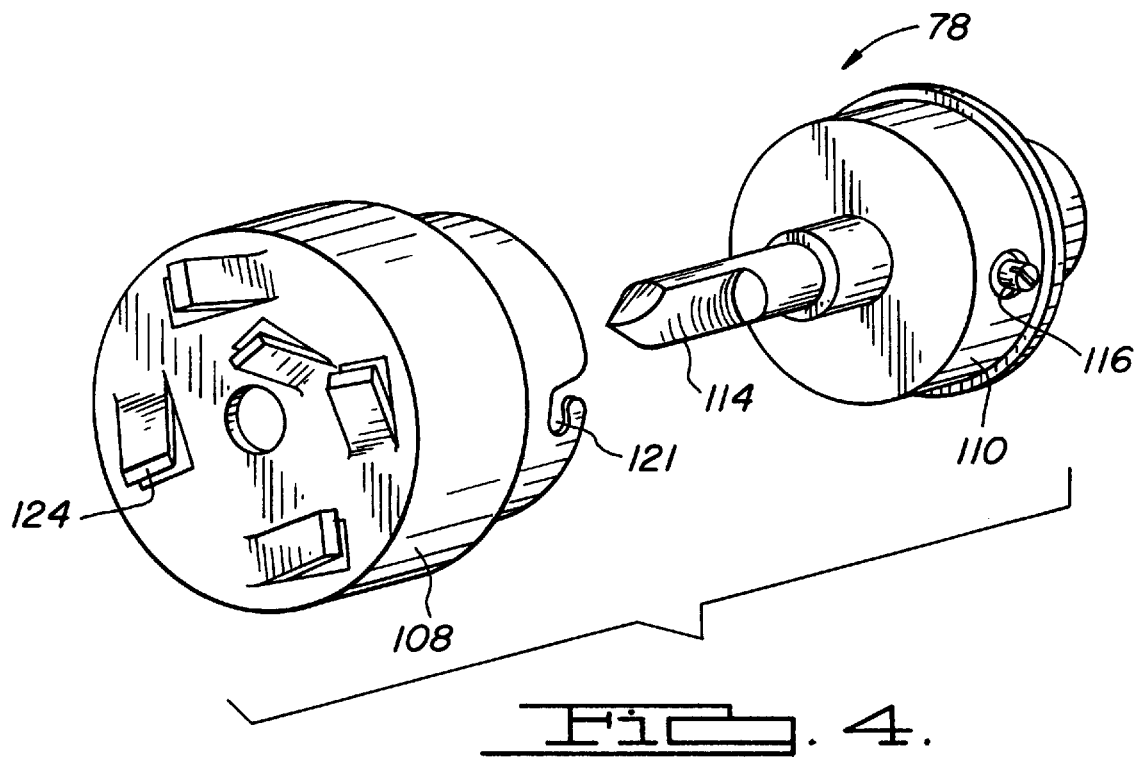
FIG. 4 is an exploded perspective view of the cutting blade assembly shown in FIG. 3 according to the teachings of the preferred embodiment of the present invention.
Figure 5:
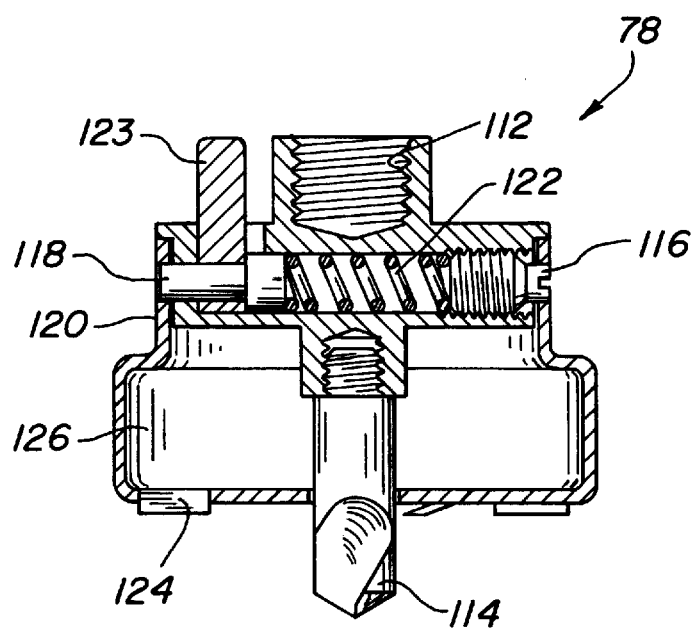
FIG. 5 is an elevational cross-sectional view of a cutting blade assembly shown in FIG. 4 according to the teachings of the preferred embodiment of the present invention.
Figure 4A:
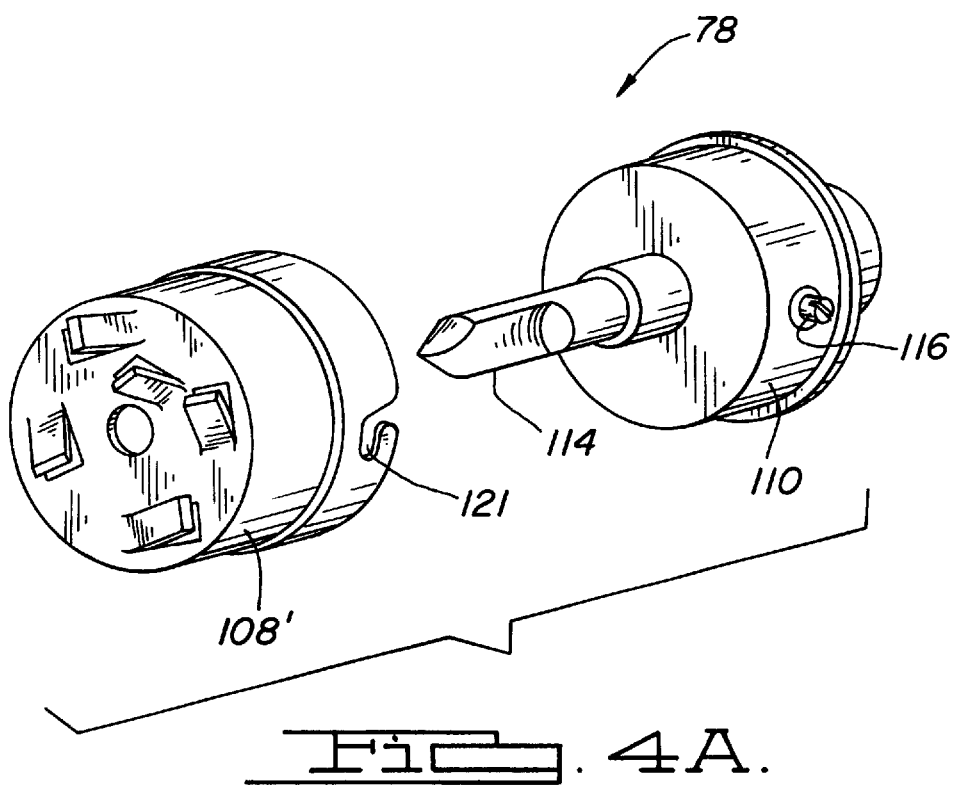
FIG. 4A is a perspective view of an optional blade member having both a diameter and a height less than that of the blade member of FIG. 4.

The cutting blade assembly 78 will now be described in greater detail with reference to FIGS. 4, 4A and 5. The cutting blade assembly 78 includes a blade member 108 and a coupling member 110. The coupling member 110 is used for securing the blade member 108 to the reamer shaft 74 by engaging the threaded portion 86 of the reamer shaft 74 with an internally threaded bore 112. The coupling member 110 includes a drill member 114 which is secured to the lower end of the coupling member 110 which is used to drill the natural patella, as well as a fixed pin member 116 and a movable pin member 118 which are used to removably attach the blade member 108 to the coupling member 110. The movable pin member 118 engages an aperture 120 in the blade member 108 while the fixed pin member 116 engages a slot 121 on the blade member 108. The coupling member 110 also includes a spring 122 which is used to bias the movable pin member 118 into engagement with the aperture 120, and a pin driver 123 which is operable to cause displacement of the movable pin member 118 so as to allow the blade member 108 to be removed from the coupling member 110. Finally, the blade member 108 has a plurality of cutting flanges 124 which are used to remove bone from the patella and to pass bone shavings into a chamber 126 formed between the blade member 108 and the coupling member 110.

As discussed above, the thickness of the cutting blade assembly 78 is selected to be different for different diameters of patellar implants. To accomplish this, the thickness of the blade member 108 varies with the diameter of the blade member 108. In particular, a blade member 108 having a greater diameter also has a greater height, while a blade member 108' (shown in FIG. 4A) having a smaller diameter is smaller in height. This permits the surgeon to select the proper measurement setting 105 by measuring only the thickness of the natural patella, without having to adjust the depth of reaming for varying thicknesses of patellar implants.

As mentioned above, the measurement settings 105 can be related to the intercondylar thickness of a selected portion of the femur as well as the thickness of the natural patella before resection. The intercondylar thickness measurement is based upon a selected portion of a resected portion of the femur or the portion about to be resected.

FIGS. 6 through 9 illustrate the femur and resected portions. One of these resected portions of the femoral resection forms the basis for the intercondylar thickness measurement. In particular, FIGS. 6 and 7 illustrate views of the distal end of a femur 128 and various resected portions. Specifically, FIG. 6 illustrates a side view of the distal end of the femur 128 showing a resected distal femoral portion 130, a resected anterior femoral condyle portion 132, and a resected anterior chamfer portion 134. As is known to those skilled in the art, additional cuts are made to the distal end of the femur 128 in preparation for receiving a prosthesis (not shown). The resected portions include a posterior femoral condyle portion and a posterior chamfer portion, neither of these portions being shown resected for the sake of simplicity.

FIG. 7 illustrates the distal end of the femur 128 partially resected. Specifically, both the distal femoral resection and the anterior femoral condyle resection have been made. The resected distal femoral condyle portion 130 is shown in spaced-apart relation from the femur 128. The resected anterior femoral portion 132 (shown in FIG. 6) is not illustrated in FIG. 7. A dotted line "ACR" identifies the line of resection for the anterior chamfer resection. Once this latter resection is made, the resected anterior chamfer portion 134 is formed.

The resected anterior chamfer portion 134, as illustrated in FIG. 6, is generally triangular in cross-section. However, as illustrated in FIG. 8, which is a top view of the resected anterior chamfer portion 134, the triangular configuration is not continuous but is interrupted by a recessed area 136 (also shown in FIG. 7). The recessed area 136 is actually defined by the upper surface of an intercondylar bridge or mass 137. The recessed area 136 includes patellar cartilage. The recessed area 136 also forms a first point for measurement of the intercondylar bone thickness, as illustrated in FIG. 9. The other point for measurement is the resected underside 138 of the resected anterior chamfer portion 134, which is also illustrated in FIG. 9. The width between the recessed area 136 and the resected underside 138 of the portion 134 is the intercondylar bone thickness, illustrated in FIG. 9 as "T—T" or the area between arrows "I-B-T". FIG. 9 also illustrates another measured width, which is the blade thickness, which is defined as "BT" or the area between the arrows "Bl-T".

The intercondylar bone thickness or T—T and the blade thickness B-T provide useful data in determining the measurement settings.

Figure 10:
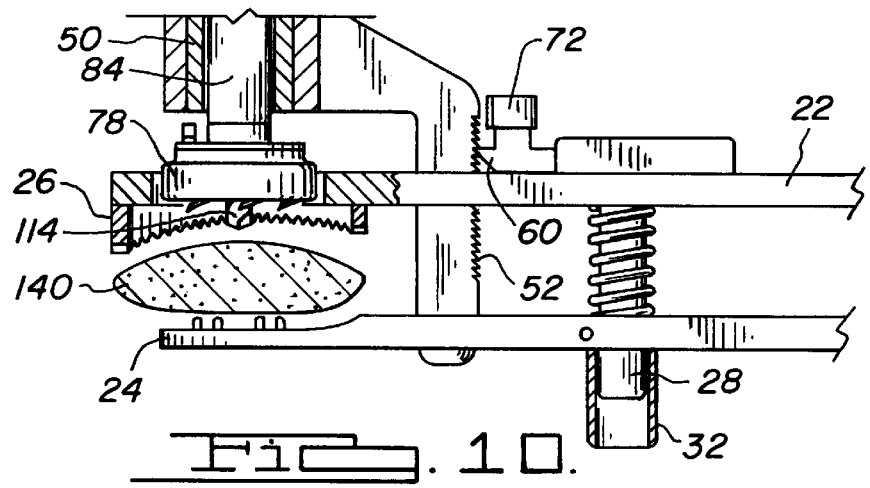
FIG. 10 is an elevational view of the patella clamp and reamer shown in FIG. 1 engaging the anterior surface of a patella according to the teachings of the preferred embodiment of the present invention.
Figure 11:
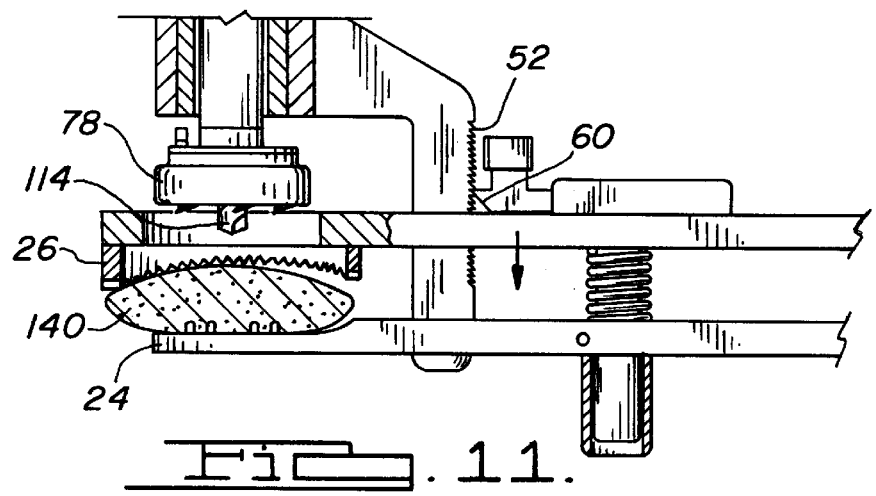
FIG. 11 is an elevational view of the patella clamp and reamer shown in FIG. 1 engaging the posterior surface of the patella and in clamped relation with the patella according to the teachings of the preferred embodiment of the present invention.
Figure 12:
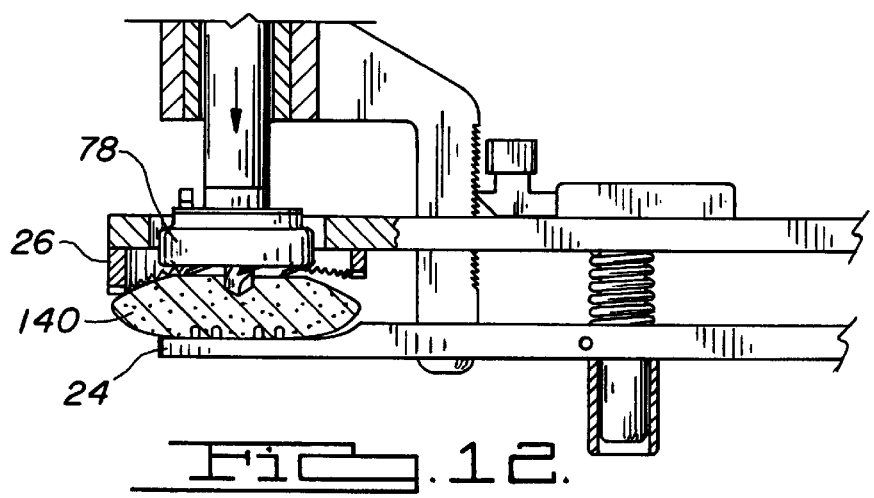
FIG. 12 is an elevational view of the cutting blade assembly being operatively positioned against the posterior surface of the patella according to the teachings of the preferred embodiment of the present invention.

The method of using the surgical instrument 10 will now be described with reference to FIGS. 10–12. The anterior contour cuts of the femur are resected prior to receiving a commercially available implant (not shown). The surgeon then preferably estimates the intercondylar thickness of the intercondylar mass 137 of the resected anterior chamfer portion 134 by measuring the thickness T—T of the portion 134 as a result of the anterior chamfer cut illustrated in FIGS. 6 and 7. After the above measurements have been made, the surgeon grips the handle portions 20 and 22 and position the concave surface 34 of the lower jaw member 24 under the anterior surface of a patella, illustrated as 140. The handle portions 20 and 22 are then driven towards one another thereby causing the upper jaw member 26 to be driven downwardly against the force of the springs 30 so as to cause the patella 140 to be gripped between the two jaw members 24 and 26.

Thereafter, the cutting blade assembly 78 is fitted to the threaded portion 86 of the reamer shaft 74. The depth adjustment head 76 is positioned relative to the reamer shaft 74, and relative to the measurement indicia, depending on how much material is to remain after the resection. In particular, the depth adjustment head 76 is adjusted to equal the thickness of the natural patella 140 plus the intercondylar thickness T—T of the resected anterior chamfer portion 134 less 2 mm. If the intercondylar thickness T—T is not equal to 3.5 mm of the thickness or the saw blade is not equal to 1.5 mm, the general formula described in Equation (1) may be used. The cutting blade assembly 78 is then attached to the reamer shaft 74 by causing engagement between the threaded portion 86 with the internally threaded bore 112. The upper end 80 of the reamer shaft 74 is then connected to a surgical drill and the reamer shaft 74 is rotated. The reamer shaft 74 is moved downward toward the patella 140 thereby causing the cutting blade assembly 78 to progressively engage and remove material from the patella 140. This downward movement of the reamer shaft 74 continues until the lower end face 92 of the depth adjustment head 76 engages the upper end face 56 of the guide head 50, whereupon the predetermined amount of bone material will be left after the resection from the patella 140. Thereafter, the cutting blade assembly 78 is removed from the reamer shaft 74 and then the patella clamp 12 is released from gripping engagement with the patella 140.

While the above detailed description describes the preferred embodiments of the present invention, it should be understood that the present invention is susceptible to modification, variation and alteration without deviating from the subjoined claims.

What is claimed is:

1. A surgical instrument for the resection of a bone, said surgical instrument comprising:

a first jaw member and a second jaw member for clamping a bone therebetween, said first jaw member including a reamer opening defined by a first sidewall having a first diameter;

a reamer for reaming the bone upon movement of said reamer with respect to said first and second jaw members;

means for guiding movement of the reamer as said reamer moves relative to said first and second jaw members, said means for guiding movement of said reamer being displaced from said first and second jaw members; and means for limiting movement of said reamer upon engagement with said means for guiding;

said reamer including a cutting blade assembly and a portion mountable for rotation within said means for guiding;

said means for guiding including an end surface and an axial bore extending from said end surface for receiving said reamer, said axial bore defined by a second sidewall having a second diameter, said first diameter being different from said second diameter; and wherein said means for limiting movement of said reamer upon engagement with said means for guiding including means for engaging and releasing said reamer so as to adjust the position of said cutting blade assembly with respect to said second jaw member.

2. The surgical instrument for the resection of a bone as set forth in claim 1, wherein said surgical instrument is operable to resect a patella.

3. The surgical instrument for the resection of a bone as set forth in claim 1, further comprising means for guiding said first jaw member and said second jaw member in a substantially parallel shiftable movement.

4. The surgical instrument for the resection of a bone as set forth in claim 1, wherein said means for guiding movement of said reamer is secured to said first jaw.

5. The surgical instrument for the resection of a bone as set forth in claim 1, wherein said portion mountable for rotation within said means for guiding includes a shaft and wherein said means for guiding movement of said reamer includes a guide body, said end surface being formed on said guide body and said axial bore being formed through said guide body.

6. The surgical instrument for the resection of a bone as set forth in claim 1, wherein said portion mountable for rotation within said means for guiding includes a shaft and wherein said cutting blade assembly includes a plurality of blades each of which are operable to mechanically communicate with said shaft, at least two of said plurality of blades having different diameters with the height of said one cutting blade assembly having a greater diameter being greater than the height of the said one cutting blade assembly having a smaller diameter.

7. The surgical instrument for the resection of a bone as set forth in claim 1, wherein said cutting blade assembly includes a blade, said surgical instrument further comprising means for locating said blade at predetermined distances from said first jaw member.

8. The surgical instrument for the resection of a bone as set forth in claim 7, wherein said means for locating said blade includes a plurality of measurement settings operable to indicate the distance to which said blade may be displaced.

9. The surgical instrument for the resection of a bone as set forth in claim 8, wherein said measurement settings are disposed on said means for locating said blade at least partially in response to the thickness of said bone.

10. The surgical instrument for the resection of a bone as set forth in claim 8, wherein said bone is a patella which is being shaped to engage the femoral component of a knee joint prosthesis, said femoral component having an intercondylar thickness, said measurement settings being disposed on said means for locating said blade at least partially in response to said intercondylar thickness of said femoral component.

11. A method for the resection of a patella prior to implantation of a prosthetic device onto a femur from which a portion has been resected, the resected portion having an intercondylar thickness, said method comprising the steps of:

forming a surgical instrument operable to resect the patella;

determining the intercondylar thickness of the resected portion of the femur; and resecting the patella to a depth at least in part determined by the intercondylar thickness of the resected portion of the femur.

12. The method for resection of a patella as set forth in claim 11, wherein said step of resecting the patella includes the step of locating a surface on said surgical instrument having a plurality of measurement settings disposed thereon, said measurement settings corresponding at least in part to the intercondylar thickness of the resected bone portion.

13. The method for resection of a patella as set forth in claim 11, wherein said step of forming a surgical instrument includes forming a surgical instrument including a first arm, a second arm operatively associated with said first arm, and a reamer having a blade which is operable to resect the patella upon movement of said reamer with respect to said first and second arms.

14. The method for resection of a patella as set forth in claim 13, including the step of resecting the patella by guiding movement of said reamer at a position displaced from said first and second arms.

15. The method for resection of a patella as set forth in claim 14, wherein said step of resecting the patella by guiding movement of said reamer includes the steps of locating a surface on said surgical instrument having a plurality of measurement settings disposed thereon, said measurement settings corresponding at least in part to the intercondylar thickness of the resected bone portion.

16. The method for resection of a patella as set forth in claim 14, including the step of clamping the patella between said first and second arms.

17. The method for resection of a patella as set forth in claim 16, wherein said step of clamping the patella between said first and second arms includes the step of guiding movement of said first and second arms in a substantially parallel relationship.

* * * * *